US010226226B2

(12) United States Patent
Fokkenrood et al.

(10) Patent No.: US 10,226,226 B2
(45) Date of Patent: Mar. 12, 2019

(54) FILTERING APPARATUS FOR FILTERING AN ULTRASOUND SIGNAL

(75) Inventors: Steven Antonie Willem Fokkenrood, 'S-Hertogenbosch (NL); Franciscus Paulus Maria Budzelaar, Eindhoven (NL); Nanad Mihajlovic, Eindhoven (NL); Erik Godefridus Antonius Harks, Rijen (NL); Szabolcs Deladi, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1303 days.

(21) Appl. No.: 13/885,403

(22) PCT Filed: Nov. 14, 2011

(86) PCT No.: PCT/IB2011/055066
§ 371 (c)(1),
(2), (4) Date: May 15, 2013

(87) PCT Pub. No.: WO2012/066462
PCT Pub. Date: May 24, 2012

(65) Prior Publication Data
US 2013/0245440 A1 Sep. 19, 2013

(30) Foreign Application Priority Data

Nov. 18, 2010 (EP) .................................... 10191687
Apr. 27, 2011 (EP) .................................... 11163905

(51) Int. Cl.
*A61B 8/12* (2006.01)
*A61B 8/08* (2006.01)
(Continued)

(52) U.S. Cl.
CPC .............. *A61B 8/12* (2013.01); *A61B 8/0883* (2013.01); *A61B 8/5269* (2013.01);
(Continued)

(58) Field of Classification Search
CPC ....... A61B 8/0883; A61B 8/5269; A61B 8/12; A61B 2017/00106; A61B 2019/462; A61B 18/1492
See application file for complete search history.

(56) References Cited

U.S. PATENT DOCUMENTS 5,409,000 A 4/1995 Imran
5,497,777 A 3/1996 Abdel-Malek et al.
(Continued)

FOREIGN PATENT DOCUMENTS

AU 2009251074 1/2010
JP 2004209066 A 7/2004
(Continued)

OTHER PUBLICATIONS

Nillesen et al. "3D Cardiac Segmentation Using Temporal Correlation of Radio Frequency Ultrasound Data." MICCAI 2009, Part II, LNCS 5762, pp. 927-934 (2009).*
(Continued)

*Primary Examiner* — Angela M Hoffa

(57) ABSTRACT

The invention relates to a filtering apparatus (15) for filtering an ultrasound signal, which is influenced by an electrical unit and comprises a first part including information about an object (4) from which the ultrasound signal has been received and a second part not comprising information about the object. A correction signal determination unit (17) determines a correction signal being indicative of the influence of the electrical unit on the ultrasound signal from the second part of the ultrasound signal and a correction unit (18) corrects the first part of the ultrasound signal based on the determined correction signal for filtering the influence of the electrical unit out of the ultrasound signal. Since the correction signal is indicative of the influence of the electrical unit, wherein the correction signal is used for correcting the (Continued)

ultrasound signal, unwanted interference visible in the unfiltered ultrasound signal can be filtered out.

14 Claims, 9 Drawing Sheets

(51) Int. Cl.
*A61B 18/14* (2006.01)
*A61B 17/00* (2006.01)
*A61B 90/00* (2016.01)

(52) U.S. Cl.
CPC . *A61B 18/1492* (2013.01); *A61B 2017/00106* (2013.01); *A61B 2090/062* (2016.02)

(56) References Cited

U.S. PATENT DOCUMENTS

| | | | |
|---|---|---|---|
| 5,553,618 | A | 9/1996 | Suzuki et al. |
| 2003/0204184 | A1 | 10/2003 | Ferek-Patric |
| 2005/0124898 | A1 | 6/2005 | Borovsky et al. |
| 2006/0100506 | A1 | 5/2006 | Halperin et al. |
| 2008/0045946 | A1* | 2/2008 | Vaska .............................. 606/49 |
| 2010/0312117 | A1 | 12/2010 | Fernandez et al. |
| 2011/0184286 | A1 | 7/2011 | Bruce et al. |
| 2012/0004547 | A1* | 1/2012 | Harks et al. .................. 600/439 |
| 2013/0231655 | A1* | 9/2013 | Budzelaar et al. ............. 606/33 |

FOREIGN PATENT DOCUMENTS

| | | |
|---|---|---|
| JP | 2008500138 A | 1/2008 |
| JP | 2009090104 | 4/2009 |
| JP | 2009261441 A | 11/2009 |
| JP | 2010240131 A | 10/2010 |
| RU | 2333011 C1 | 9/2008 |
| WO | WO2006032058 | 3/2006 |
| WO | WO2010082146 | 7/2010 |

OTHER PUBLICATIONS

A.W.M. Van Den Enden, "Efficiency in Multirate and Complex Digital Signal Processing", published in 2001, Chapter 7.1.

Z. Huang et al., "On Ultrasound Image Reconstruction by Tissue Density Estimation", 2010 8th IEEE International Conference on Control and Automation, Xiamen, China, Jun. 9-11, 2010, pp. 767-772.

M.M. Nillesen et al., "3D Cardiac Segmentation Using Temporal Correlation of Radio Frequency Ultrasound Data", MICCAI, Jan. 2009, 2 pages.

* cited by examiner

FILTERING APPARATUS FOR FILTERING AN ULTRASOUND SIGNAL

FIELD OF THE INVENTION

The invention relates to a filtering apparatus, a filtering method and a filtering computer program for filtering an ultrasound signal. The invention relates further to an ultrasound sensing apparatus, an ultrasound sensing method and an ultrasound sensing computer program for sensing an object.

BACKGROUND OF THE INVENTION

U.S. Pat. No. 5,409,000 discloses an ablation catheter with an ultrasound transducer and an ablation electrode. Ultrasound waves are coupled into cardiac tissue and ultrasound echoes, which return from the cardiac tissue, are picked up by the ultrasound transducer and visualized on a screen. A physician performing an ablation procedure can observe the resulting ultrasound image on the screen, in order to perform the ablation procedure depending on the ultrasound image. The ablation procedure is performed by applying radio frequency (RF) current to an ablation electrode located at the tip of the ablation catheter.

A disadvantage of RF ablation together with ultrasound imaging inside the same catheter is the capacitive and/or conductive coupling of the RF signal onto the ultrasound signal generated by the ultrasound transducer and used for forming the ultrasound image. This reduces the quality of the ultrasound signal and, thus, of the ultrasound image used for monitoring the ablation procedure.

SUMMARY OF THE INVENTION

It is an object of the present invention to provide a filtering apparatus, a filtering method and a filtering computer program for filtering an ultrasound signal, wherein the influence of an electrical unit like an RF ablation electrode can be reduced. It is a further object of the present invention to provide an ultrasound sensing apparatus for sensing an object, which comprises the filtering apparatus, and a corresponding ultrasound sensing method and ultrasound sensing computer program for sensing an object.

In a first aspect of the present invention a filtering apparatus for filtering an ultrasound signal is presented, wherein the ultrasound signal is influenced by an electrical unit and comprises a first part comprising information about an object from which the ultrasound signal has been received and a second part not comprising information about the object, wherein the filtering apparatus comprises:

- a correction signal determination unit for determining a correction signal being indicative of the influence of the electrical unit on the ultrasound signal from the second part of the ultrasound signal,
- a correction unit for correcting the first part of the ultrasound signal based on the determined correction signal for filtering the influence of the electrical unit out of the ultrasound signal.

Since the correction signal determination unit determines a correction signal being indicative of the influence of the electrical unit, which is, for example, an RF ablation electrode, on the ultrasound signal from the second part, which does not comprise information about the object, the correction signal is caused by, for example, unwanted effects like capacitive and/or conductive coupling of an electrical signal from the electrical unit onto the ultrasound signal. The first part of the ultrasound signal comprises both, information about the object and information about unwanted effects like the capacitive and/or conductive coupling. By correcting the first part of the ultrasound signal based on the determined correction signal for filtering the influence of the electrical unit out of the ultrasound signal, the desired information about the object is more pronounced and easier retrievable from the first part of the ultrasound signal. The quality of the ultrasound signal is therefore improved.

Preferentially, the electrical unit is an electrode for applying electrical energy, in particular, RF energy, to the object, wherein the influence on the ultrasound signal is caused by capacitive and/or conductive coupling. In a preferred embodiment, the electrical unit is an RF ablation electrode. The object is preferentially a heart of a person or of an animal, in particular, a heart wall, and the information about the object, which is comprised by the ultrasound signal, is preferentially information about the cardiac tissue.

The ultrasound signal is preferentially an A-line signal, wherein the first part of the A-line comprises information about the object and the second part of the A-line does not comprise information about the object.

It is preferred that the correction unit is adapted to subtract the determined correction signal from the first part of the ultrasound signal for correcting the first part of the ultrasound signal.

It is further preferred that the filtering apparatus comprises a fundamental frequency providing unit for providing a fundamental frequency of the influence by the electrical unit, wherein the correction signal determination unit is adapted to determine a sub-part of the second part of the ultrasound signal, which corresponds to at least one cycle of the influence by the electrical unit, depending on the provided fundamental frequency, and to determine the correction signal depending on the determined sub-part of the second part of the ultrasound signal, and wherein the correction unit is adapted to subtract the correction signal from the first part of the ultrasound signal for correcting the first part. Such a correction of the first part of the ultrasound signal further improves the quality of correcting the first part. For example, a sequence of the determined sub-parts of the second part of the ultrasound signal can be determined as the correction signal.

In a preferred embodiment the fundamental frequency providing unit is adapted to determine the fundamental frequency by cross correlating two consecutive sub-parts of the second part of the ultrasound signal. In particular, the fundamental frequency providing unit is preferentially adapted to fit a parabolic function to the cross correlation and to determine the fundamental frequency depending on the maximum of the fitted parabolic function. This allows determining the fundamental frequency for the current ultrasound signal, in particular, for the current A-line, in a relatively simple way. In another embodiment, the fundamental frequency providing unit can be adapted to receive the fundamental frequency from the control unit for controlling the electrical unit and to provide the received fundamental frequency to the correction signal determination unit.

In a preferred embodiment the correction signal determination unit is adapted to upsample the sub-part of the second part. Preferentially, the correction signal determination unit is adapted to upsample the sub-part of the second part by a factor of two. It is further preferred that the correction signal determination unit is adapted to apply an infinite impulse response (IIR) filter to the upsampled sub-part of the second part. In particular, the correction signal determination unit is adapted to apply a bi-reciprocal IIR filter to the upsampled sub-part of the second part.

It is preferred that the correction signal determination unit is adapted to perform following steps several times: a) upsampling the sub-part of the second part by a factor of two, and b) applying an IIR filter to the upsampled sub-part of the second part. The upsampling and the application of the IIR filter is preferentially performed four times, but can also be performed more than four times. The upsampling of the sub-part of the second part and the application of, for example, a bi-reciprocal IIR filter allows generating an upsampled sub-part of the second part such that aliasing does not occur and the sub-part of the second part is unaffected. The preferred factor of two per upsampling step allows an easy implementation on digital signal processors, which can be useful when integrating the calculations on-chip.

It is further preferred that a time dependent amplification has been applied to the ultrasound signal, wherein the correction signal determination unit is adapted to apply the time dependent amplification also to the correction signal. The time-dependent amplification (time-gain-control or TGC) allows compensating for losses in the intensity of ultrasound pulses due to attenuation within the object. This compensation improves the quality of the ultrasound signal and, thus, of the finally filtered ultrasound signal, which may be used, for example, for monitoring an ablation procedure, in particular, for determining an ablation depth within the ablated object.

In a further aspect of the present invention an ultrasound sensing apparatus for sensing an object is presented, wherein the ultrasound sensing apparatus comprises:

a catheter including an ultrasound unit for generating an ultrasound signal depending on ultrasound waves received from the object and a further unit being an electrical unit, wherein the ultrasound unit and the electrical unit are adapted to operate simultaneously, wherein the generated ultrasound signal is influenced by the electrical unit and includes a first part comprising information about the object from which the ultrasound signal has been received and a second part not comprising information about the object, a filtering apparatus as defined in claim 1, wherein the correction signal determination unit is adapted to determine a correction signal being indicative of the influence of the electrical unit on the generated ultrasound signal from the second part of the ultrasound signal and wherein the correction unit is adapted to correct the first part of the ultrasound signal based on the determined correction signal for filtering the influence of the electrical unit out of the first part of the ultrasound signal.

In a further aspect of the present invention a filtering method for filtering an ultrasound signal is presented, the ultrasound signal being influenced by an electrical unit and comprising a first part comprising information about an object from which the ultrasound signal has been received and a second part not comprising information about the object, wherein the filtering method comprises:

determining a correction signal being indicative of the influence of the electrical unit on the ultrasound signal from the second part of the ultrasound signal by a correction signal determination unit, correcting the first part of the ultrasound signal based on the determined correction signal for filtering the influence of the electrical unit out of the ultrasound signal by a correction unit.

In a further aspect of the present invention an ultrasound sensing method for sensing an object is presented, wherein the ultrasound sensing method comprises:

generating an ultrasound signal depending on ultrasound waves received from the object by an ultrasound unit, wherein the ultrasound unit and a further unit being an electrical unit are included in a catheter, wherein the ultrasound unit and the electrical unit operate simultaneously and wherein the generated ultrasound signal is influenced by the electrical unit and includes a first part comprising information about the object from which the ultrasound signal has been received and a second part not comprising information about the object, the filtering steps of the filtering method as defined in claim 12, wherein the correction signal determination unit determines a correction signal being indicative of the influence of the electrical unit on the generated ultrasound signal from the second part of the ultrasound signal and wherein the correction unit corrects the first part of the ultrasound signal based on the determined correction signal for filtering the influence of the electrical unit out of the first part of the ultrasound signal.

In a further aspect of the present invention a filtering computer program for filtering an ultrasound signal is presented, wherein the filtering computer program comprises program code means for causing a filtering apparatus as defined in claim 1 to carry out the steps of the filtering method as defined in claim 12, when the filtering computer program is run on a computer controlling the filtering apparatus.

In a further aspect of the present invention an ultrasound sensing computer program for sensing an object is presented, wherein the ultrasound sensing computer program comprises program code means for causing an ultrasound sensing apparatus as defined in claim 10 to carry out the steps of the ultrasound sensing method as defined in claim 13, when the ultrasound sensing computer program is run on a computer controlling the ultrasound sensing apparatus.

It shall be understood that the filtering apparatus of claim 1, the ultrasound sensing apparatus of claim 10, the filtering method of claim 12, the ultrasound sensing method of claim 13, the filtering computer program of claim 14 and the ultrasound sensing computer program of claim 15 have similar and/or identical preferred embodiments as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
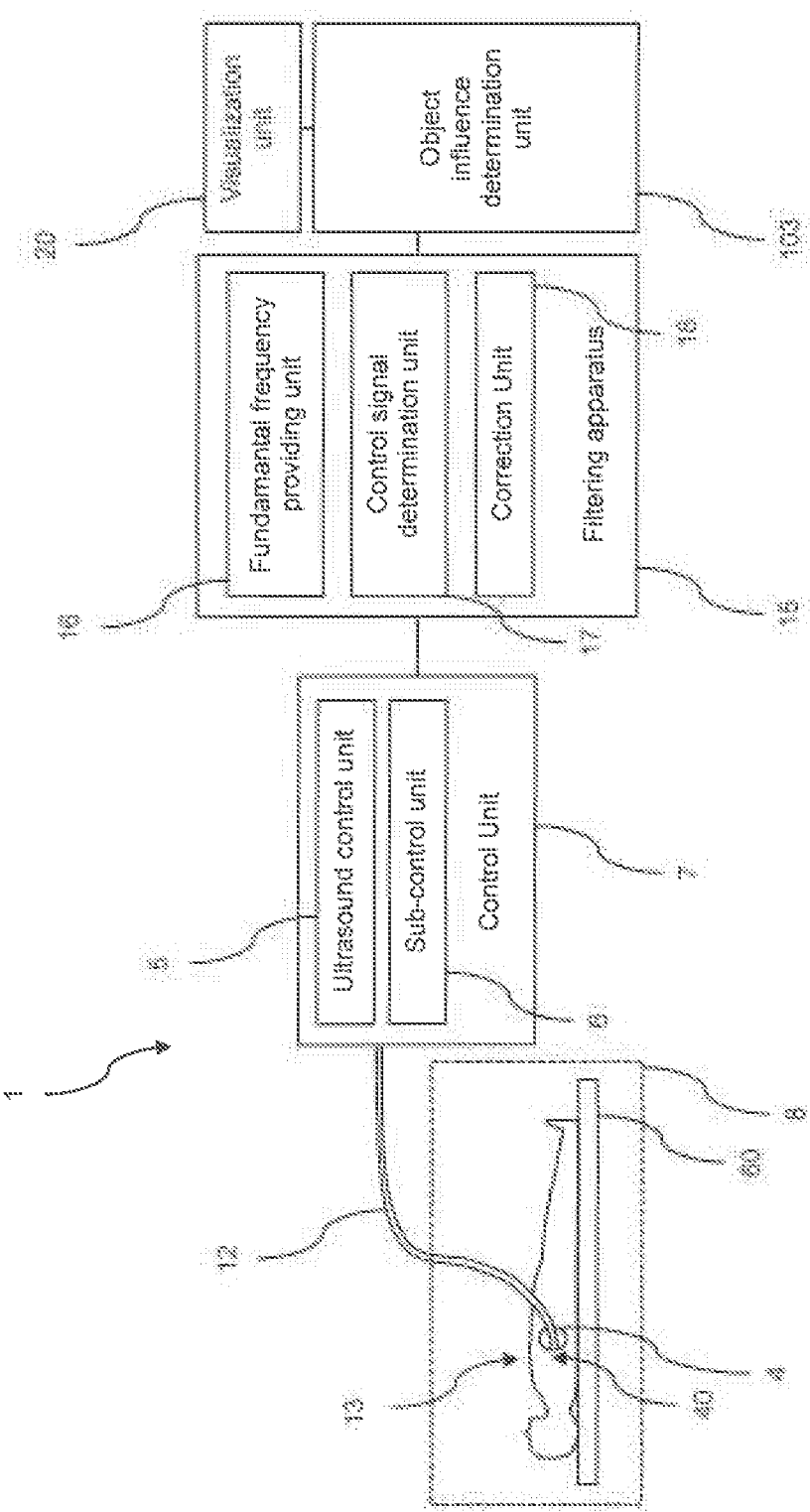
FIG. 1 shows schematically and exemplarily an embodiment of an ultrasound sensing apparatus for sensing an object.
Figure 2:
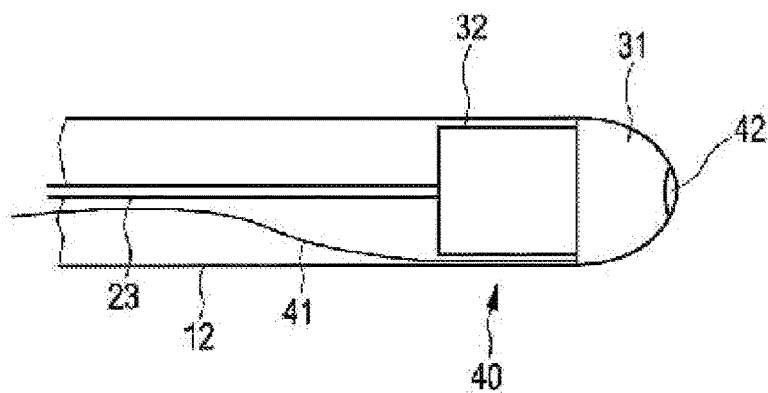
FIG. 2 shows schematically and exemplarily a tip of a catheter of the ultrasound sensing apparatus.

FIG. 1 shows schematically and exemplarily an ultrasound sensing apparatus 1 for sensing an object 4. In this embodiment, the object 4 is a heart of a person 13 located on a table 60. In particular, the object is cardiac tissue of a wall of the heart 4. The ultrasound sensing apparatus 1 comprises a catheter 12 with a catheter tip 40, which is schematically and exemplarily shown in more detail in FIG. 2.

The catheter tip 40 comprises an ultrasound unit 32 for generating an ultrasound signal depending on ultrasound waves received from the object 4. The catheter tip 40 further comprises a further unit 31 being an electrical unit. The electrical unit 31 is adapted to apply electrical energy to the cardiac tissue.

The ultrasound unit 32 is controlled by an ultrasound control unit 5, wherein the ultrasound unit 32 and the ultrasound control unit 5 are adapted to send out ultrasound pulses into the cardiac tissue, to receive dynamic echo series after the ultrasound pulses have been reflected by the cardiac tissue and to generate an ultrasound signal depending on the received dynamic echo series. The ultrasound unit 32 is connected with the ultrasound control unit 5 via an electrical connection 23.

The electrical energy application unit 31 is an ablation electrode for applying electrical RF energy to the cardiac tissue, wherein the ablation electrode 31 is connected with a sub-control unit 6 via an electrical connection 41 being, for example, a cable for controlling the ablation electrode 31. The ablation electrode 31 is a cap electrode provided at the tip 40 of the catheter 12 and comprises a frontal, central opening 42 for allowing the ultrasound unit 32 to sense the cardiac tissue through the opening 42.

The sub-control unit 6 and the ultrasound control unit 5 are integrated in a control unit 7. In other embodiments, the control units can be separate control units. Furthermore, the sub-control unit 6 is preferentially further adapted to control a steering of the catheter tip 40 and/or an irrigation. In this case, the catheter further comprises a steering element and/or an irrigation element, respectively, which are not shown in FIG. 1 and FIG. 2. The different control functions can be performed by any number of control units, for example, by a single control unit or by two or more than two control units.

The control unit 7 is adapted to operate the ultrasound unit 32 and the electrical unit 31 simultaneously, wherein the generated ultrasound signal is influenced by the electrical unit 31, i.e., in this embodiment, by the application of the RF energy. The generated ultrasound signal 19 is schematically and exemplarily shown in FIG. 3.

Figure 3:
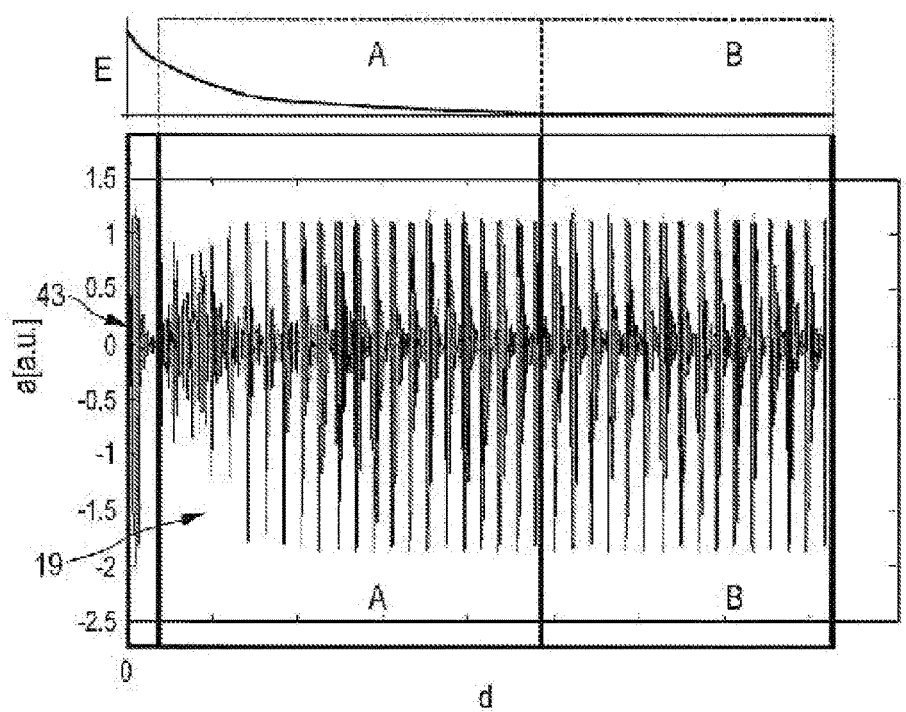
FIG. 3 shows schematically and exemplarily a dependence of ultrasound energy depending on tissue depth and a corresponding ultrasound signal.

FIG. 3 shows in the upper part schematically and exemplarily the ultrasound energy E depending on the tissue depth d. The lower part of FIG. 3 shows the generated ultrasound signal 19. In particular, the ultrasound signal 19 shown in the lower part of FIG. 3 is an A-line, wherein the amplitude is shown depending on the tissue depth d. The ultrasound energy E decreases with increasing tissue depth d because of the absorption and scattering by the cardiac tissue. The first part A of the ultrasound signal 19 corresponds to an ultrasound energy E, which is larger than 0. The first part A comprises therefore information about the cardiac tissue from which the ultrasound signal 19 has been received. The second part B of the ultrasound signal 19 corresponds to an ultrasound energy E being substantially 0. The second part B of the ultrasound signal 19 does therefore not comprise information about the object. In this example, the first part A comprises tissue information, which is shadowed by RF interference, and the second part B does not comprise tissue information due to absorption and scattering of ultrasound energy, and only RF interference is visible in the second part B. To both parts of the ultrasound signal 19 a time-dependent amplification has been applied (TGC). The first part 43 of the ultrasound signal 19 is caused by transducer ring down.

The ultrasound sensing apparatus 1 further comprises a filtering apparatus 15 for filtering the generated ultrasound signal 19. The filtering apparatus 15 comprises a fundamental frequency providing unit 16 for providing a fundamental frequency of the influence by the RF ablation electrode 31. In this embodiment, the fundamental frequency providing unit 16 is adapted to determine the fundamental frequency by cross-correlating two consecutive sub-parts of the second part B of the ultrasound signal 19. Preferentially, the fundamental frequency providing unit 16 is adapted to fit a parabolic function to the cross-correlation and to determine the fundamental frequency depending on the maximum of the fitted parabolic function. This will in the following be described in more detail.

It is assumed that the ultrasound signal comprises several samples $S_k$, wherein a first sub-part X can be defined by following equation:

$$X=[S_{i\ldots j}], \quad (1)$$

wherein i denotes the first sample of the second part B of the ultrasound signal, which may be, in this example, 3000 (i=3000) and wherein $$j=i+N. \quad (2)$$

The variable N is chosen such that it comprises at least one full RF cycle, which is defined by the sub-control unit 6, in particular, by an RF generator of the sub-control unit 6, to be 460 kHz±20 kHz, in this embodiment. Moreover, in this embodiment the ultrasound signal is acquired at a frequency of 200 MHz. Thus, N=454 (200 MHz divided by 440 kHz) samples include one RF cycle. The variables can therefore be defined as i=3000 and j=3454. Of course, if in another example the RF specified by the RF generator is different, the number of samples including a full RF cycle will change accordingly.

A second consecutive sub-part of the second part B of the ultrasound signal can be defined by following equation:

$$Y=[S_k \ldots] \quad (3)$$

with $$k=j+1 \quad (4)$$

and $$l=k+N. \quad (5)$$

The consecutive sub-parts X and Y are cross-correlated, a parabolic fit equation is fitted to the resulting cross-correlation and the maximum of the parabolic fit equation defines the fundamental frequency.

In other words, for each A-line a fundamental RF frequency can be extracted by cross-correlation of two consecutive parts $X=[S_{t-2W-1} \ldots {}_{t-W-1}]$ and $Y=[S_{t-W} \ldots {}_{t}]$, wherein the window size W is optimized to contain at least one full period of RF interference. Pre-knowledge about the frequency and about the frequency band of RF, which may be obtainable from the specification of the RF generator, can improve the speed of the cross-correlation calculation, because an adequate window size can be determined as described above. The variable t is preferentially chosen such that t−2W defines a sample representing RF interference only and no tissue reflections.

In a further embodiment, the sub-parts defined in equations (1) and (3) can be upsampled and the upsampled sub-parts can be cross correlated. In this case, the fundamental RF frequency is preferentially determined directly from the cross correlation, without performing a parabolic fit.

The filtering apparatus 15 further comprises a correction signal determination unit 17 for determining a correction signal being indicative of the influence of the electrical unit 31 on the ultrasound signal 19 from the second part B of the ultrasound signal 19. In particular, the correction signal determination unit 17 is adapted to determine a sub-part of the second part of the ultrasound signal, which corresponds to at least one cycle of the influence by the electrical unit 31, depending on the provided fundamental frequency, and to determine a sequence of the determined sub-parts of the second part of the ultrasound signal as the correction signal. A sub-part of the second part can be regarded as a template RF pattern from the A-line. This template RF pattern is chosen such that it is surely in a region of the A-line, in which only RF interference is present without tissue reflections. For example, for an ultrasound center frequency of 20 MHz the template RF pattern may be chosen at a relatively high tissue depth being larger than, for example, 15 mm.

The correction signal determination unit 17 is preferentially further adapted to upsample the template RF pattern by a factor of two and to apply a bi-reciprocal IIR filter which is an interpolation filter, to the upsampled template RF pattern. This upsampling and filtering with the bi-reciprocal IIR filter is preferentially performed several times, in particular four times. The upsampling is preferentially performed by inserting a 0 between each pair of samples of the template RF pattern, i.e. of the template RF pattern. The bi-reciprocal IIR filtering, also known as half-bandwidth recursive filtering or Mth band recursive filtering, is disclosed in, for example, ":efficiency in multirate and complex digital signal processing", A. W. M. van den Enden, ISBN 90-6674-650-5, Chapter 7.1, which is herewith incorporated by reference.

The bi-reciprocal IIR filter is adapted in such a way that aliasing does not occur and the template RF pattern is unaffected. The upsampling by a factor of two in a single upsampling step followed by the filtering is preferred, because it is easy to implement on Digital Signal Processors (DSPs), which can be very useful when integrating on-chip. In another embodiment, the upsampling can also be performed by another factor and/or another interpolation filter can be used.

In the above described example with the sampling at 200 MHz, a complete RF cycle has 454 samples, if an RF frequency of 460 kHz+/−20 kHz is assumed. However, the RF frequency and its harmonics can change during ablation. This change is not necessarily an integer number of samples, i.e., for example, the RF frequency can change from 460,000.000 Hz to 460,000.005 Hz within two consecutive RF cycles inside a single A-line. The template may therefore not exactly match a respective sub-part of the part A, if the correction signal is used for correcting the first part A. In order to improve the matching accuracy, a fractional shift in samples could therefore be provided. However, if an upsampling is performed with an upsampling factor of, for example, 16 as described above, the resolution is increased to 0.0625 samples, i.e., if before upsampling the distance between consecutive samples was one, this distance is now 0.0625. It has been found that this resolution is enough to compensate for the RF frequency change within a single A-line.

The correction signal determination unit 17 can further be adapted to recalculate the RF fundamental frequency to a fractional frequency in samples. For example, if the location of the maximum of the polynomially interpolated correlation is known from the above described fitting procedure, the RF fundamental frequency for the respective A-line is known. The recalculation can be performed such that the determined RF fundamental frequency fits to the upsampling by the factor of preferentially 16, which was achieved as described above by performing the upsampling by a factor of two four times. The RF fundamental frequency can be recalculated to the nearest sample, i.e. the RF fundamental frequency can be rounded to the nearest sample. For example, if the determined RF fundamental frequency is 454.05 samples, it can be recalculated to 454.0625 samples.

The ultrasound unit control unit 5 is preferentially adapted to apply a time dependent amplification to the ultrasound signal. The correction signal determination unit 17 is therefore preferentially adapted to apply the same time dependent amplification to the correction signal. The correction signal determination unit 17 is therefore preferentially adapted to compensate the correction signal, i.e. the upsampled and filtered template RF patterns, for amplitude modification.

The filtering apparatus 15 further comprises a correction unit 18 for correcting the first part A of the ultrasound signal 19 based on the determined correction signal for filtering the influence of the electrical unit 31 out of the ultrasound signal 19. In particular, the correction unit 18 is adapted to subtract the determined correction signal from the first part A of the ultrasound signal 19.

The subtraction of the correction signal, i.e. the sequence of upsampled template RF patterns, from the first part A of the ultrasound signal 19 can be described by following equation:

$$C_{i-Rm \ldots i-R(m-1)}^{subA} = O_{i-Rm \ldots i-R(m-1)}^{subA} - T_{delay:U:UR+delay}^{subB} \qquad (6)$$

with $$delay = Um(R - \lfloor R \rfloor) \qquad (7)$$

In equation (6) $C_{i-Rm \ldots i-R(m-1)}^{subA}$ denotes a corrected sub-part of the first part A comprising the samples defined by i−Rm ... i−R(m−1), wherein R is the fundamental RF frequency after the floor function has been applied to the fundamental RF frequency, m varies from 0 to i/R, and i denotes the first beginning of the second part B as defined above with reference to equation (1). Moreover, $O_{i-Rm \ldots i-R(m-1)}^{subA}$ denotes the sub-part of the first part A before being corrected, and $T_{delay:U:UR+delay}^{subB}$ denotes samples of the upsampled and filtered template RF patterns forming the correction signal. The samples of the upsampled and filtered template RF pattern are defined by delay:U:UR+delay, i.e. by $$\text{delay}, \text{delay}+U, \text{delay}+2U, \ldots, UR+\text{delay},$$

wherein U denotes the total upsampling factor, which is, in the above described example with four times upsampling with a factor of two, 16. Thus, from the template RF pattern $T_{delay:U:UR+delay}^{subB}$ only each U-th sample is taken, because of the total upsampling factor U.

Thus, the correction signal is subtracted from the original A-line data containing both, ultrasound tissue reflection and RF interference.

Figure 4:
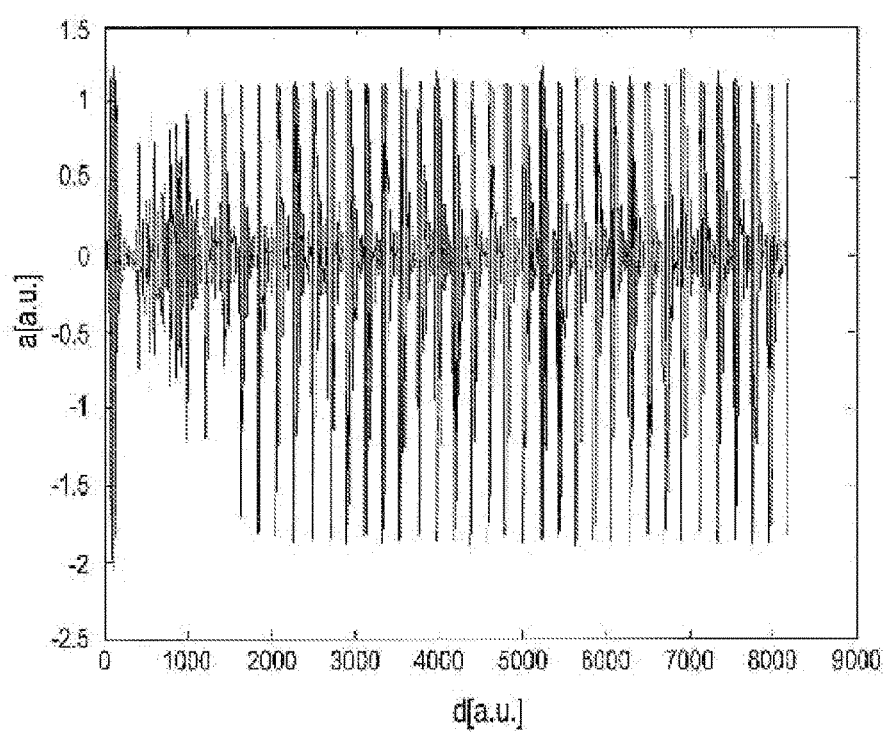
FIG. 4 shows schematically and exemplarily an unfiltered A-line.
Figure 5:
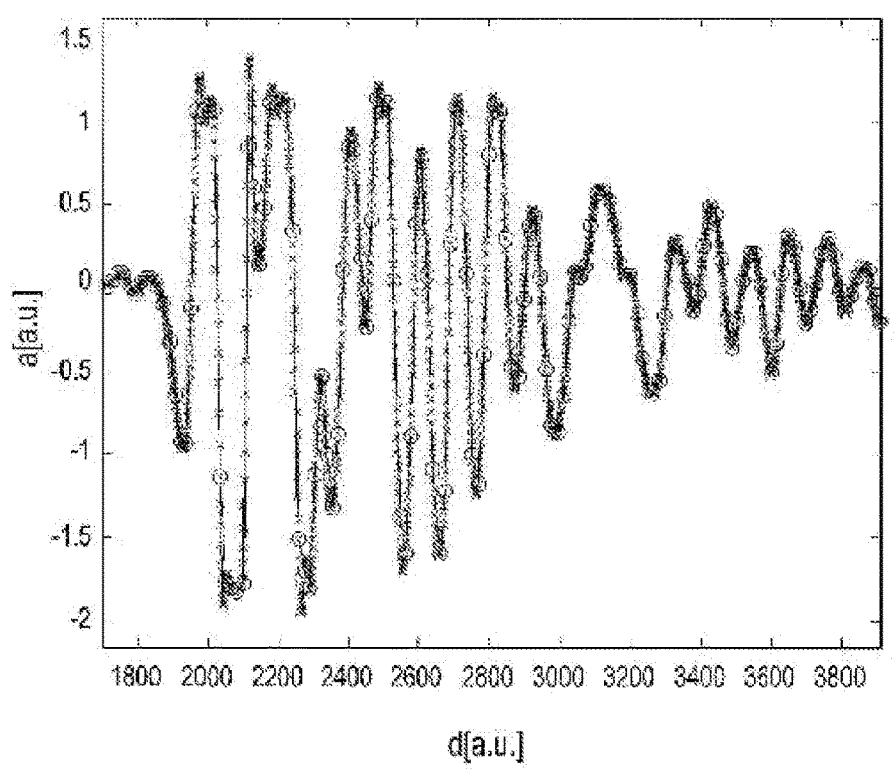
FIG. 5 illustrates the effect of upsampling and filtering.

FIG. 4 shows schematically and exemplarily a single A-line with RF interference. FIG. 5 shows schematically and exemplarily a sub-part of the second part B for illustrating the upsampling and filtering. The original samples are indicated by the circles, and the upsampled samples are indicated by crosses. The sub-part shown in FIG. 4 comprises about 2000/16 samples with respect to the original sampling, if the total upsampling factor is 16, so about a quarter of the template having 454 samples with respect to the original sampling in the above described embodiment. In FIG. 5, the high amplitude between 2000 and 3000 is half of the actual RF interference cycle. Whereas RF interference occurs at zero crossings, and the RF cycle is a sine, there are two almost, but not identical RF interferences per RF cycle.

Figure 6:
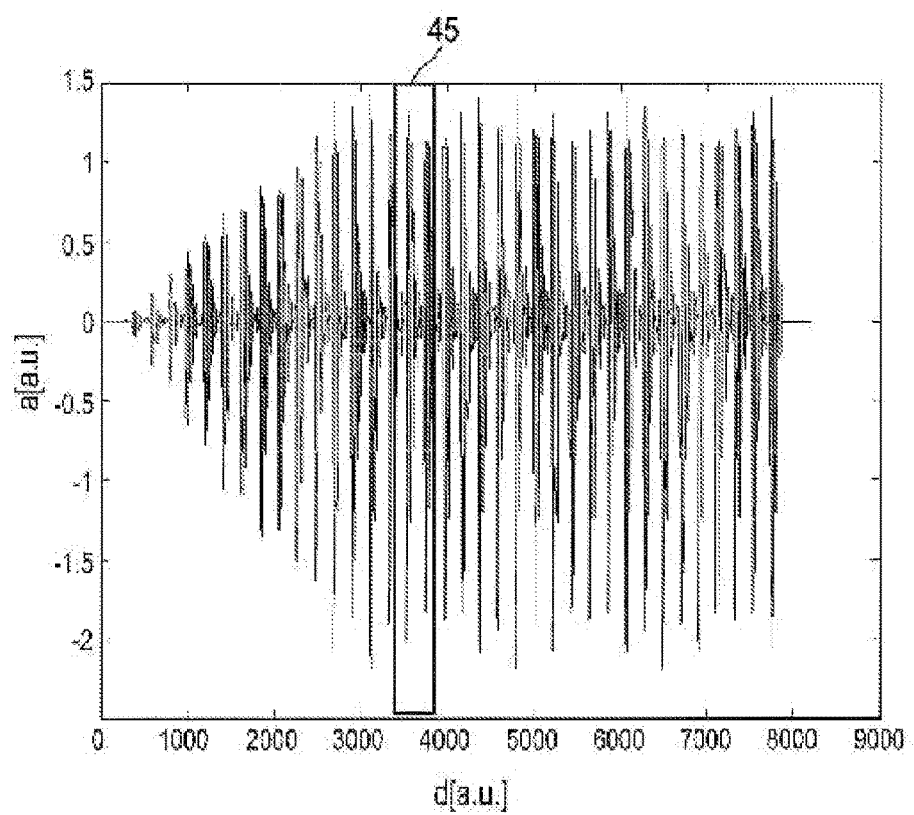
FIG. 6 shows schematically and exemplarily a correction signal.
Figure 7:
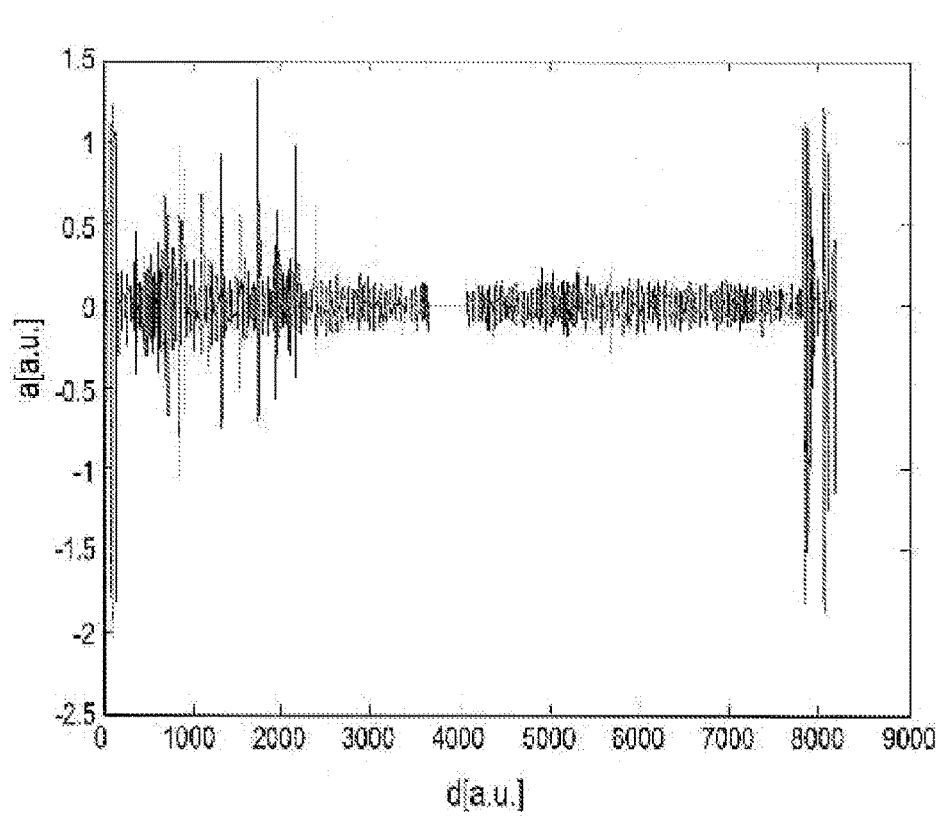
FIG. 7 shows schematically and exemplarily a corrected A-line.

FIG. 6 shows schematically and exemplarily a reconstructed RF interference pattern, i.e. a sequence of RF templates matching the A-line, which can be subtracted from the A-line. The formation of the sequence of RF templates and the subtraction is preferably only performed for the first part A of the ultrasound signal. A single template RF pattern is indicated by box 45. The consecutive patterns forming the correction signal shown in FIG. 6 vary, because different samples of the upsampled template RF patterns are used for the subtraction in accordance with equation (6).

Figure 8:
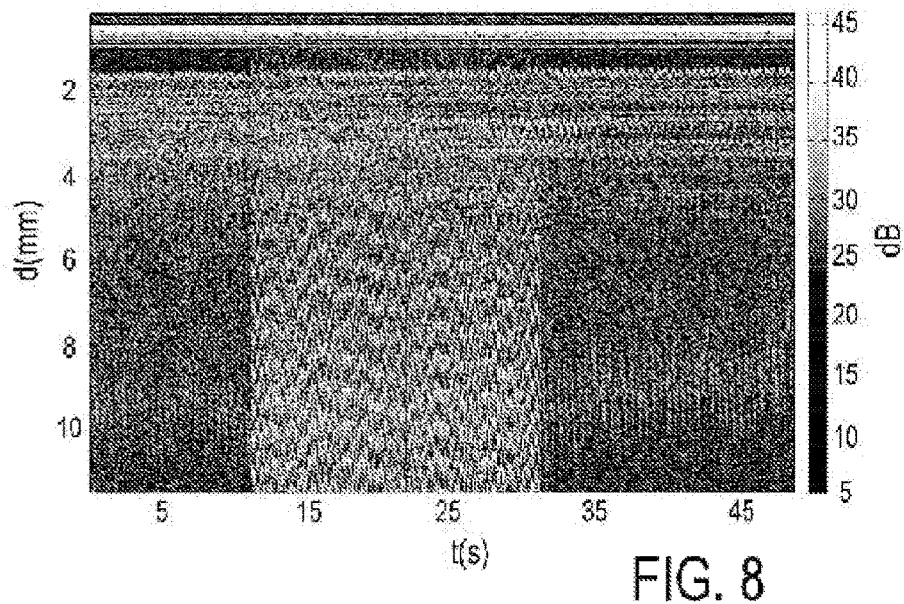
FIG. 8 shows an ultrasound M-mode image comprised of non-corrected A-lines.
Figure 9:
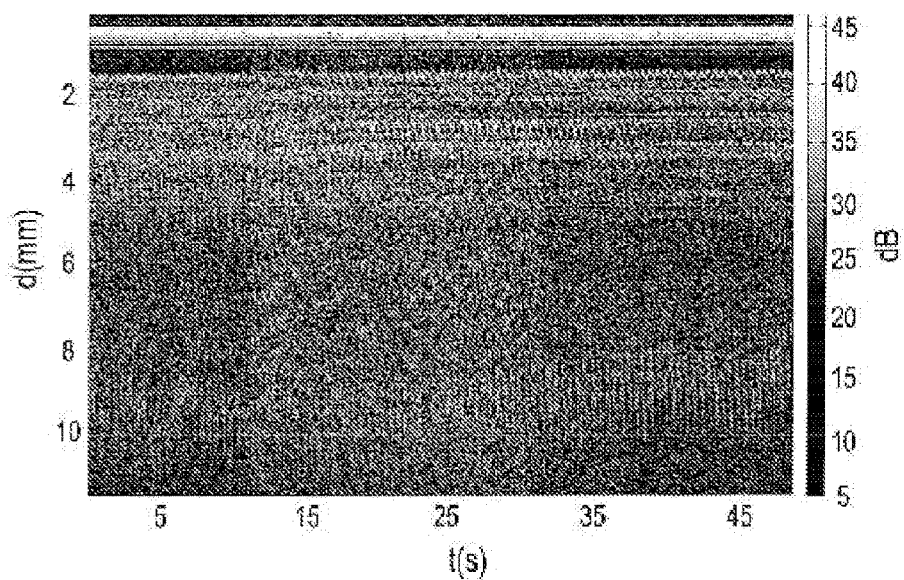
FIG. 9 shows an ultrasound M-image comprised of corrected A-lines.

The correction signal is subtracted at each point in time in the A-line, at least in the first part A of the A-line, where RF interference is occurring. The resulting A-lines can be stuck together to form an M-mode ultrasound image. FIG. 8 shows such an M-mode ultrasound image without performing the above described correction and FIG. 9 shows the M-mode ultrasound image after having performed the correction. As can be clearly seen, RF interference is reduced in the M-mode ultrasound image shown in FIG. 9.

Referring again to FIG. 1, the ultrasound sensing apparatus 1 further comprises an object influence determination unit 103 for determining the influence of the energy application on the object 4 depending on the ultrasound sensing of the object 4. In particular, the energy application unit 31 is adapted to ablate the object 4, wherein the object influence determination unit 103 is adapted to determine an ablation depth, which may also be regarded as being a lesion boundary, depending on the ultrasound sensing of the object 4. The object influence determination unit 103 is therefore adapted to receive an ultrasound signal from the ultrasound unit 5 and to determine the ablation depth depending on the received ultrasound signal. The determination of the ablation depth and also of a heart wall thickness based on an M-mode ultrasound image is described in, for example, WO 2010/082146 A1, which is herewith incorporated by reference. For example, the object influence determination unit 103 can be adapted to determine the position of a front surface and a back surface of the heart wall from the ultrasound signal and to determine the thickness of the heart wall depending on these positions, i.e. the corresponding depth positions can be subtracted from each other to determine the thickness of the heart wall.

The sub-control unit 6 is preferentially adapted to control the ablation electrode 31 depending on the ablation depth determined by the object influence determination unit 103. For example, the power and/or duration of applying ablation energy to the object 4 are controlled depending on the determined ablation depth. In particular, the object influence determination unit 103 can be adapted to determine the thickness of the heart wall, and the sub-control unit 6 can then be adapted to control the ablation electrode 31 depending on this determined thickness and the determined ablation depth. Preferentially, the sub-control unit 6 is adapted to ablate the heart wall tissue until a desired degree of transmurality of the heart wall tissue is reached, in particular, until the resulting lesion is transmural.

Preferentially, the ultrasound sensing apparatus 1 is adapted to determine the thickness of the heart wall and the ablation depth repeatedly, wherein the ablation depth determination unit 103 is adapted to determine repeatedly a degree of transmurality of ablation from the determined thickness and the determined ablation depth. In particular, the ultrasound sensing apparatus 1 is adapted to terminate an ablation procedure, if a predetermined degree of transmurality of ablation has been reached.

The ultrasound sensing apparatus 1 further comprises a visualization unit 20 for visualizing the ablation depth. In particular, the visualization unit 20 is adapted for visualizing the progression of a lesion boundary. The visualization is preferentially performed in real-time. The visualization unit 20 is preferentially adapted to show the ultrasound signal, the progression of ablation, i.e. the lesion boundary, and the front and back surface positions.

The ultrasound sensing apparatus 1 is preferentially used in combination with a system for determining the position and/or orientation of the catheter 12, in particular, within the object 4, preferably, within a heart of a human being or an animal. In this embodiment, an imaging system like a magnetic resonance image system or an X-ray fluoroscopy system is used for determining the position and/or orientation of the catheter. This imaging system is indicated by the broken line 8 shown in FIG. 1. The catheter 12, in particular, the catheter tip can comprise elements for facilitating the determination of the orientation and/or position of the catheter by using the imaging system 8. For example, the catheter tip can comprise a tracking coil, if the catheter tip is used within a magnetic resonance imaging system, or elements that can be identified on an X-ray image and that are shaped such that a determination of the position and/or orientation of the catheter by using an X-ray fluoroscopy system is possible. The catheter tip can also comprise a location sensor for determining the position and/or orientation of the catheter 12, in particular, of the catheter tip within the object 4.

The positioning systems allows a user to position the catheter 12 within the heart, or more specifically, in the left atrium, of a patient. The user can position the catheter 12 in the correct position with respect to the heart wall to measure the wall thickness using the ultrasound signal generated by the ultrasound unit 11 and the object influence determination unit 103. By using the determined position of the catheter it is possible to display the thickness of the heart wall in an image of the heart. After collecting sufficient measurements, i.e. after determining the thickness of the heart wall at different locations on the heart wall, the user can then establish an ablation strategy including required power and duration depending on the determined heart wall thickness.

It is also possible to use the catheter tip for tracing over the prior-performed ablation lesions for verification purposes. The continuity and depth of the lesions that have been created can be determined.

Figure 10:
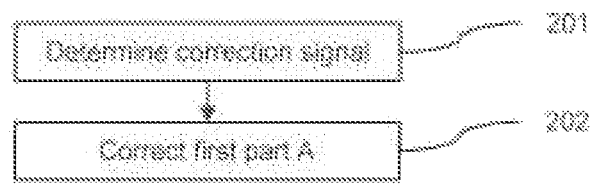
FIG. 10 shows a flowchart exemplarily illustrating an embodiment of a filtering method for filtering an ultrasound signal.

In the following embodiment of a filtering method for filtering an ultrasound signal will exemplarily be described with reference to a flowchart shown in FIG. 10.

An ultrasound signal can be influenced by an electrical unit and comprising a first part comprising information about an object from which the ultrasound signal has been received and a second part not comprising information about the object has been provided. In step 201, a correction signal being indicative of the influence of the electrical unit on the ultrasound signal is determined from the second part of the ultrasound signal by a correction signal determination unit. In step 202, the first part of the ultrasound signal is corrected based on the determined correction signal for filtering the influence of the electrical unit out of the ultrasound signal by a correction unit.

Figure 11:
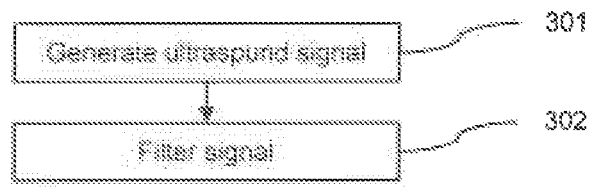
FIG. 11 shows a flowchart exemplarily illustrating an embodiment of an ultrasound sensing method for sensing an object.

FIG. 11 shows a flowchart exemplarily illustrating an embodiment of an ultrasound sensing method for sensing an object.

In step 301, an ultrasound signal is generated depending on ultrasound waves received from the object by an ultrasound unit, wherein the ultrasound unit and the further unit being an electrical unit are included in a catheter, wherein the ultrasound unit and the electrical unit operate simultaneously and wherein the generated ultrasound signal is influenced by the electrical unit and includes a first part comprising information about the object from which the ultrasound signal has been received and a second part not comprising information about the object. In step 302, the filtering steps of the filtering method described above with reference to FIG. 10 are performed, wherein the correction signal determination unit determines a correction signal being indicative of the influence of the electrical unit on the generated ultrasound signal from the second part of the ultrasound signal and wherein the correction unit corrects the first part of the ultrasound signal based on the determined correction signal for filtering the influence of the electrical unit out of the first part of the ultrasound signal.

The filtering apparatus preferentially provides a digital filter, based on sample rate conversion, for filtering out RF without affecting the ultrasound signal. This digital filter can be applied in realtime and thus allows the visualization of unperturbed ultrasound signals, which can be processed and/or shown during, for example, a medical procedure.

In an integrated ablation and ultrasound monitoring catheter both ultrasound sensing as well as ablation are performed. Although separate wiring is used for both signals, the RF signals which are very large in power, can couple indirectly onto the ultrasound wiring. This coupling can occur inside the catheter via capacitive coupling, because shielding is insufficient, or inside the heart due to conductive coupling via, for example, blood and/or saline irrigation fluid. Normally RF frequencies of, for example, about 450 to 500 kHz are outside the band of interest in ultrasound imaging, which is generally between about 1 and 50 MHz. However, harmonics and noise are present, which can lead to interference patterns at constant intervals in the ultrasound signal where the sinusoidal shape crosses DC level. The low amplitude ultrasound signal can therefore be masked by this RF interference.

In medical imaging, ultrasound transducers of various frequencies are being used up to about 50 MHz. For lesion monitoring with integrated RF ablation and ultrasound monitoring ultrasound transducers with a center frequency between about 20 to 30 MHz are preferentially used. In order to obtain a high resolution, ultrasound signals are acquired at high frequency of, for example, 200 MHz per A-line. A-lines are typically sampled at 20-100 Hz to get an M-mode image, but higher sampling rates up to, for example, 1 kHz are also possible. Several different filtering techniques can be used to filter RF, but they should work in realtime, i.e. processing of many samples per second should be possible. The above described filtering apparatus can be adapted to remove the RF interference from the ultrasound signal in real-time without affecting the quality of the ultrasound signal. Moreover, the corresponding algorithm is preferentially optimized to run on specific hardware chips, in particular, on DSP processors.

Although in the above described embodiments, the correction signal is used for correcting the first part A of the ultrasound signal, the correction signal can also be used to correct the entire ultrasound signal including the first part A and the second part B.

Although in the above described embodiments certain processing steps for processing an RF template have been described, in other embodiments also other processing steps can be performed. For example, a FIR implementation of a fractional delay filter can be used instead of the bi-reciprocal IIR interpolation filter. Moreover, also a standard IIR interpolation filter, which is not bi-reciprocal, can be used.

Although in the above described embodiments the electrical unit, which influences the ultrasound signal, is an ablation electrode, in other embodiments the electrical unit can also be another unit such as an x-ray imaging unit or an electrical knife, which may cause interference and/or noise.

The ultrasound sensing apparatus and the filtering apparatus are preferentially adapted to be used in tissue imaging during treatment of, for example, cardiac arrhythmias, or tumor ablation, wherein RF ablation and ultrasound imaging are combined in a single catheter or a single needle. The algorithm implemented in the filtering apparatus can be useful for removing also other interferences with similar characteristics as RF interferences from signals of interest.

Although the ultrasound sensing apparatus is preferentially adapted as a cardiac ablation monitoring catheter which can be used in combination with an RF signal generator, the ultrasound sensing apparatus can also be adapted to sense other objects like other parts of a person or of an animal such as another organ or vessels, or a technical object like a pipeline. Moreover, instead of applying RF energy, the electrical unit can also be adapted to apply other electrical energy to the object.

Although in the embodiment described above with reference to FIG. 2 the catheter comprises an electrical unit being an ablation electrode and an ultrasound unit only, the catheter can also comprise further elements like further sensing elements and/or further energy application elements, irrigation elements, et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Calculations like the calculation of the fundamental RF frequency, the determination of the correction signal, the correction of the first part of the ultrasound signal depending on the correction signal, et cetera performed by one or several units or devices can be performed by any other number of units or devices. For example, the determination of the fundamental RF frequency, the determination of the correction signal, the correction of the ultrasound signal depending on the determined correction signal, the determination of, for example, the ablation depth depending on the corrected ultrasound signal, et cetera can be performed by a single unit or by any other number of different units. The calculations and/or the control of the filtering apparatus in accordance with the filtering method and/or the control of the ultrasound sensing apparatus in accordance with the ultrasound sensing method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a filtering apparatus for filtering an ultrasound signal, which is influenced by an electrical unit and comprises a first part including information about an object from which the ultrasound signal has been received and a second part not comprising information about the object. A correction signal determination unit determines a correction signal being indicative of the influence of the electrical unit on the ultrasound signal from the second part of the ultrasound signal and a correction unit corrects the first part of the ultrasound signal based on the determined correction signal for filtering the influence of the electrical unit out of the ultrasound signal. Since the correction signal is indicative of the influence of the electrical unit, wherein the correction signal is used for correcting the ultrasound signal, unwanted interference visible in the unfiltered ultrasound signal can be filtered out.

The invention claimed is:

1. A filtering apparatus for filtering an ultrasound signal, the ultrasound signal (19) being influenced by an electrical unit and comprising a first part (A) comprising information about an object (4) from which the ultrasound signal (19) has been received and a second part (B) not receiving the ultrasound signal from the object and not comprising information about the object (4), characterized in that the filtering apparatus (15) comprises:
a correction signal determination unit (17) configured to determine a correction signal being indicative of the influence of the electrical unit on the ultrasound signal (19) from the second part (B) of the ultrasound signal (19),
a correction unit (18) configured to correct the first part (A) of the ultrasound signal (19) based on the determined correction signal for filtering the influence of the electrical unit (31) out of the ultrasound signal (19).

2. The filtering apparatus as defined in claim 1, wherein the correction unit (18) is configured to subtract the determined correction signal from the first part (A) of the ultrasound signal (19).

3. The filtering apparatus as defined in claim 2, wherein the filtering apparatus (15) comprises a fundamental frequency providing unit (16) configured to provide a fundamental frequency of the influence by the electrical unit,
the correction signal determination unit (17) is configured to determine a sub-part of the second part of the ultrasound signal, which corresponds to at least one cycle of the influence by the electrical unit, depending on the provided fundamental frequency, and to determine the correction signal depending on the determined sub-part of the second part (B) of the ultrasound signal.

4. The filtering apparatus as defined in claim 3, wherein the fundamental frequency providing unit (16) is configured to determine the fundamental frequency by cross correlating two consecutive sub-parts in time of the second part (B) of the ultrasound signal (19).

5. The filtering apparatus as defined in claim 3, wherein the correction signal determination unit (17) is configured to upsample the sub-part of the second part (B).

6. The filtering apparatus as defined in claim 5, wherein the correction signal determination unit (17) is configured to apply an infinite impulse response (IIR) filter to the upsampled sub-part of the second part (B).

7. The filtering apparatus as defined in claim 5, wherein the correction signal determination unit (17) is configured to apply a bi-reciprocal infinite impulse response (IIR) filter to the sub-part of the second part (B).

8. The filtering apparatus as defined in claim 5, wherein the correction signal determination unit (17) is configured to perform following steps several times:
upsampling the sub-part of the second part (B) by a factor of two,
applying an IIR filter to the upsampled sub-part of the second part (B).

9. The filtering apparatus as defined in claim 1, wherein a time dependent amplification has been applied to the ultrasound signal and wherein the correction signal determination unit (17) is configured to apply the time dependent amplification also to the correction signal.

10. An ultrasound sensing apparatus for sensing an object, the ultrasound sensing apparatus (1) comprising:
a catheter (12) including an ultrasound unit (32) for generating an ultrasound signal (19) depending on ultrasound waves received from the object (4) and a further unit (31) being an electrical unit, wherein the ultrasound unit (32) and the electrical unit (31) are adapted to operate simultaneously, wherein the generated ultrasound signal (19) is influenced by the electrical unit (31) and includes a first part (A) comprising information about the object (4) from which the ultrasound signal (19) has been received and a second part (B) not receiving the ultrasound signal from the object and not comprising information about the object (4),
a filtering apparatus (15) comprising a correction signal determination unit (17) configured to determine a correction signal being indicative of the influence of the electrical unit (31) on the generated ultrasound signal (19) from the second part (B) of the ultrasound signal (19) and a correction unit (18) configured to correct the first part (A) of the ultrasound signal (19) based on the determined correction signal for filtering the influence of the electrical unit (31) out of the first part (A) of the ultrasound signal (19).

11. The ultrasound sensing apparatus as defined in claim 10, wherein the electrical unit (31) is an electrode for applying electrical energy to the object (4).

12. A filtering method for filtering an ultrasound signal, the ultrasound signal (19) being influenced by an electrical unit and comprising a first part (A) comprising information about an object (4) from which the ultrasound signal (19) has been received and a second part (B) not receiving the ultrasound signal from the object and not comprising information about the object (4), characterized in that the filtering method comprises:

determining a correction signal being indicative of the influence of the electrical unit on the ultrasound signal (19) from the second part (B) of the ultrasound signal (19) by a correction signal determination unit (17), correcting the first part (A) of the ultrasound signal (19) based on the determined correction signal for filtering the influence of the electrical unit (31) out of the ultrasound signal (19) by a correction unit (18).

13. A computer program product comprising a non-transitory computer readable medium having encoded thereon a filtering computer program for filtering an ultrasound signal, characterized in that the filtering computer program when executed by a processor performs the steps of:

for an ultrasound signal (19) being influenced by an electrical unit and comprising a first part (A) comprising information about an object (4) from which the ultrasound signal (19) has been received and a second part (B) not receiving the ultrasound signal from the object and not comprising information about the object (4), determining a correction signal being indicative of the influence of the electrical unit on the ultrasound signal (19) from the second part (B) of the ultrasound signal (19) by a correction signal determination unit (17), correcting the first part (A) of the ultrasound signal (19) based on the determined correction signal for filtering the influence of the electrical unit (31) out of the ultrasound signal (19) by a correction unit (18).

14. A computer program product comprising a non-transitory computer readable medium having encoded thereon An ultrasound sensing computer program for sensing an object, characterized in that the ultrasound sensing computer program comprises program code means for generating an ultrasound signal (19) depending on ultrasound waves received from the object (4) by an ultrasound unit (32), wherein the ultrasound unit (32) and a further unit (31) being an electrical unit are included in a catheter (12), wherein the ultrasound unit (32) and the electrical unit (31) operate simultaneously and wherein the generated ultrasound signal (19) is influenced by the electrical unit (31) and includes a first part (A) comprising information about the object (4) from which the ultrasound signal (19) has been received and a second part (B) not receiving the ultrasound signal from the object and not comprising information about the object (4)

determining a correction signal being indicative of the influence of the electrical unit on the ultrasound signal (19) from the second part (B) of the ultrasound signal (19) by a correction signal determination unit (17), correcting the first part (A) of the ultrasound signal (19) based on the determined correction signal for filtering the influence of the electrical unit (31) out of the ultrasound signal (19) by a correction unit (18).

* * * * *